US00PP09240P

United States Patent [19]

Ito

[11] Patent Number: Plant 9,240

[45] Date of Patent: Aug. 15, 1995

[54] NECTARINE TREE 'SUMMER JIM'

[75] Inventor: Tracy Ito, Reedley, Calif.

[73] Assignee: Ito Packing Co., Reedley, Calif.

[21] Appl. No.: 287,291

[22] Filed: Aug. 8, 1994

[51] Int. Cl.[6] ..... A01H 5/00

[52] U.S. Cl. ..... Plt./41.1

[58] Field of Search ..... Plt. 41.1

[56] References Cited

U.S. PATENT DOCUMENTS

P.P. 8,534 1/1994 Chiamori ..... Plt./41.1

*Primary Examiner*—James R. Feyrer

*Attorney, Agent, or Firm*—Dennis B. Haase

[57] ABSTRACT

A new and distinct nectarine tree, which is a sport of the tree 'Red Jim', which is distinctly similar to the parent tree but which differs therefrom in having fruit which fully ripens and is mature for harvest 10 days prior to that of the parent tree. The new tree, denominated 'Summer Jim', produces nectarines having flesh which is yellow except at the stone well where it blends to red, has cling stone fruit with highly colored exterior, and has a conspicuous distinctive yellow suture stripe.

1 Drawing Sheet

BACKGROUND OF THE VARIETY

The present invention relates to a new and distinct variety of nectarine tree, which I refer to as 'Summer Jim'. The fruit is a yellow-fleshed, cling stone type, highly colored and attractive in appearance and maturing in mid-July, which was discovered as a bud sport on a Red Jim nectarine tree, U.S. Plant Pat. No. 4,518.

ORIGIN AND ASEXUAL REPRODUCTION OF THE NEW VARIETY

At the time of my discovery of the sport, referred to above, one limb bearing the fruit of the new variety was observed growing on a Red Jim nectarine tree in a ten acre orchard located near Dinuba, in the County of Tulare, State of California. Buds of the new tree were first used to change the variety of a dehorned 'Lovell' tree and were eventually used to produce 20 trees of the new variety. The sport limb and a series of asexually reproduced trees have been regularly monitored and found to be distinctly different from their parent 'Red Jim' tree. Moreover, these new trees are stable and identical to the originally discovered sport in virtually all distinguishing characteristics, the most notable of which is an early maturing date, which is approximately ten days prior to 'Red Jim'.

SUMMARY OF THE VARIETY

The fruit of the new variety is large and displays generally uniform colors early. The fruit fully ripens about ten days before Red Jim, thereby providing an early and profitable entry on the market. When the fruit is mature, the skin thereof is predominantly bright red over yellow and a prominent yellow suture stripe, which appears earlier and shows signs of fading. The fruit begins to color earlier than the Red Jim and continues to darken until fully ripe. The fruit keeps well on the tree, thus providing for a long harvest period. Fruit held on the tree until eating ripe has more acid than the parent Red Jim. The high red coloring and the good keeping qualities make the new variety especially desirable for commercial fruit productions.

BRIEF DESCRIPTION OF THE DRAWING

The accompanying drawing illustrates typical specimens of the fruit and foliage of my new variety, as grown in the San Joaquin Valley of California. One specimen is shown in cross-section for purposes of illustrating the stone and flesh thereof, two other specimens are shown in mutually inverted relation for illustrating size, form and skin coloring; and the foliage is shown to illustrate typical leaf size, form and glandular characteristics of my new variety.

DETAILED DESCRIPTION

The following is a detailed description of my new variety with color reference being to the Maerz and Paul Dictionary of Colors, except in instances where terminology having generally accepted meaning is employed.

Parentage: Red Jim sport limb.

Propagation: Maintains its distinguishing characteristics through several bud grafts.

Locality where grown and observed: Near Dinuba, County of Tulare, Calif.

TREE

Size: Medium, vigorous; spreading, productive and regular bearer.

Trunk:

*Size.*—Medium size, average diameter.

*Surface texture.*—Medium, regular texture.

*Color.*—Similar to Red Jim; Grey (7-A-9).

Branches: Medium size; medium texture.

*Lenticels.*—Moderately large, present throughout branching. Number: Numerous. Size: 2×4–5 mm., moderately large.

Leaves:

*Average length.*—150 to 160 mm; average width of 40–42 mm.

*Color.*—Upper, page 67, Plate 22, K-7, Spinach Green; Lower, page 63, Plate 20, L-9, Eden Green.

*Shape.*—Lanceolate.

*Margin.*—Finely serrate.

*Petiole.*—Length of 10 mm; thickness of 2 mm.

*Stem glands.*—Number: Two (2). Arrangement: Opposite. Size: Small. Type: Reniform. Color: Green.

*Stipules.*—None.

Flower Bud: Large, plump.

Flowers: Large, showy.

*Color.*—Pink.

*Date of Full Bloom.*—With variety Red Jim (U.S. Plant Pat. No. 4,518) Bloom is about three days before Red Jim, with first bloom observed on Feb. 27, 1994 and full bloom achieved on Mar. 12, 1994, as opposed to Red Jim which reached full bloom on Mar. 16, 1994.

*Anthers.*—Red.

*Pollen.*—Abundant; yellow in color.

FRUIT

Maturity:

*When described.*—Firm ripe — Jul. 16, 1993 and on Jul. 16, 1994.

*Date of first picking.*—*Jul.* 16, 1993. First pick in 1994 was Jul. 16, as opposed to Red Jim which had a first pick of Aug. 2, 1994.

*Date of last picking.*—Aug. 1, 1993. Last pick in 1994 was July 24, and last pick may overlap with first pick of Red Jim by one or two days.

Size: Average, 48–50 pick size i.e., in a 7 inch box, 48 to 50 fruit may be packed in two layers.

*Uniformity.*—Uniform, slightly asymmetrical with one side being slightly longer than the other, as viewed in section.

*Diameter.*—64–67 mm.

*Transverse in suture plane.*—64–68 mm.

*Transverse at right angles to suture plane.*—72–74 mm.

Form:

*Uniformity.*—Uniform.

*Symmetrical or asymmetric.*—Oblong with equal sides.

*Suture.*—Has suture stripe similar to Red Jim variety (U.S. Plant Pat. No. 4,518) with the stripe disappearing when fruit is eating ripe. Length: 95–100 mm. Position: A shallow depression through, with slight depression near pistil point. It is a very bright colored line.

Ventral surface: Smooth, with the length of the sides differing perceptibly.

Stem cavity: Acute, 18×22×12 mm deep.

Apex: Pointed with pistil point.

Pistil point: Pronounced.

Skin:

*Thickness.*—Medium.

*Texture.*—Medium.

*Tendency to crack.*—None.

*Color.*—Ground, page 43, Plant 6, 1–6, Mellow Glow; Blush, page 37, Plate 7, H-6, Peony. The reddish over color of the fruit, which is almost identical to Red Jim, is not only a solid blush, but appears variously as striations, speckles, dapples and mottles, with the red over color tending to become darker as the fruit fully matures.

*Pubescence.*—None.

Flesh:

*Color.*—Page 43, Plate, 6, 1–6, Mellow Glow.

*Surface of pit cavity.*—Rough.

*Color of pit well.*—page 39, Plate 8, J-6, Briarwood.

*Amygladin.*—Slight.

*Juice.*—Juicy.

*Flavor.*—Good.

*Aroma.*—Pleasing.

*Texture.*—Firm and meaty.

*Fibers.*—Abundant, coarse, tough.

*Ripening.*—Even.

*Eating quality.*—Good.

Stone:

*Adherence to flesh.*—Cling.

*Fibers.*—Long over the entire pit.

*Size.*—42 mm long, 26 mm in breadth, 20 mm thick.

*Form.*—Oblong.

*Color.*—Page 39, Plate 8, J-6, Briarwood.

*Base.*—Straight.

*Sides.*—Equal, pitted near base, ridged near apex.

*Ridges.*—Slightly jagged.

*Size of position of grooves.*—Narrow from middle to base.

*Dorsal edge.*—Wide with shallow groove.

*Ventral edge.*—Thick.

*Splitting tendency.*—None.

Use: Fresh market.

Keeping quality: Good.

Shipping quality: Good.

Resistance to disease: Good.

Although this novel variety of nectarine tree possesses the described characteristics primarily as a result of the growing conditions in the Dinuba area of Tulare County, Calif., in the central portion of the San Joaquin Valley, it is to be understood that variations in the usual magnitude in characteristics incident to growing conditions, fertilization, pruning and pest control are to be expected.

Having thus described and illustrated my new nectarine tree, what is new and desired to be secured by letters Patent is:

1. A new and distinct variety of nectarine tree with fruit of yellow-fleshed cling stone type, with reddish over color of not only a solid blush, but appearing variously as striations, speckles, dapples and mottles, with the red over color tending to become darker at full maturity, substantially as herein shown and described, having a maturity period in the mid-season, having fruit of average sie with high red coloring, initially displaying a prominent yellow suture stripe which tends to fade upon full maturity and providing a long harvest period by virtue of its keeping quality on the tree.

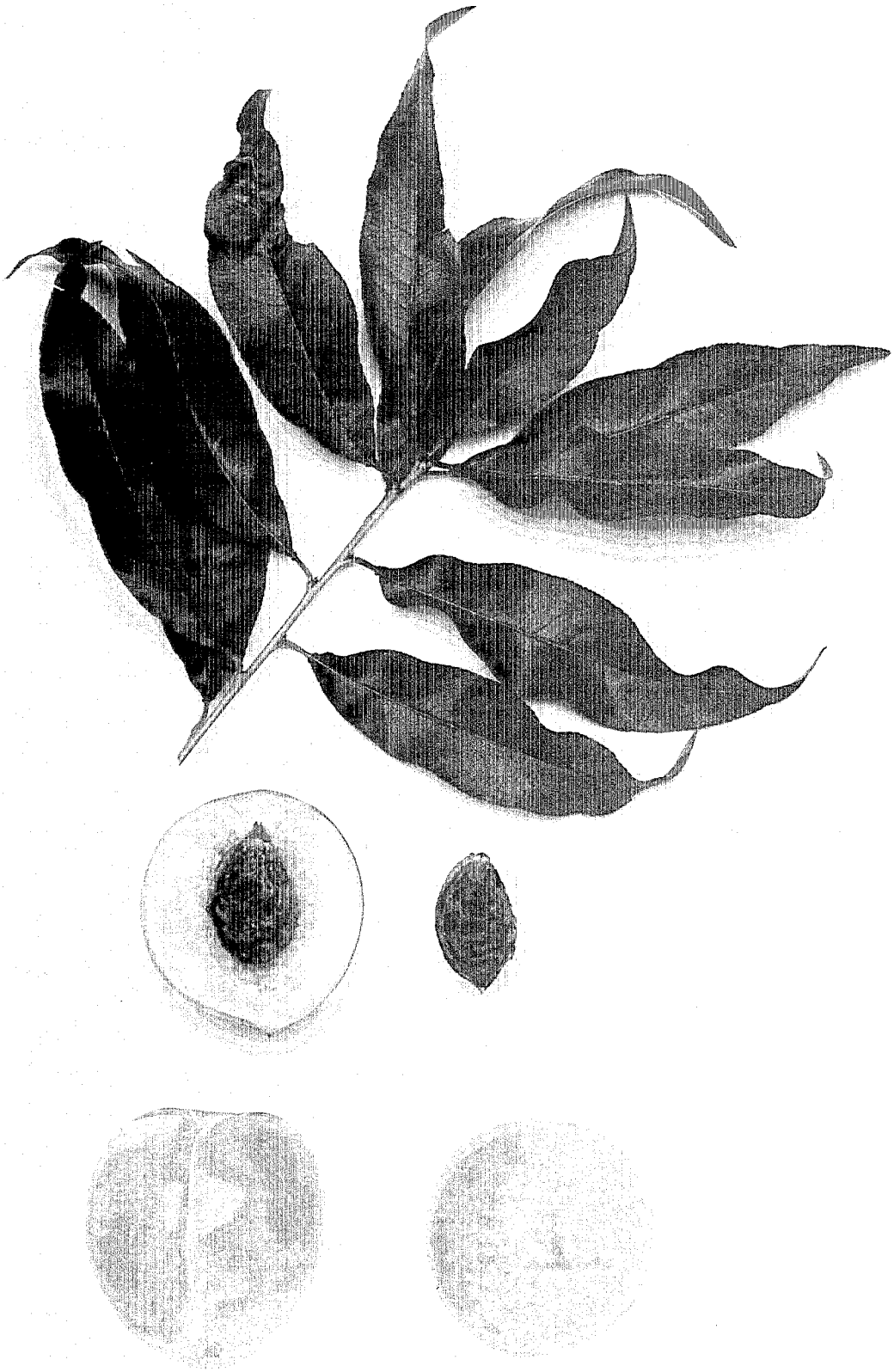

* * * * *